United States Patent
Dai et al.

(10) Patent No.: US 7,354,702 B2
(45) Date of Patent: *Apr. 8, 2008

(54) PROCESSING TISSUE TO PRODUCE A BIOPOLYMER SCAFFOLD FOR TISSUE ENGINEERING

(75) Inventors: Jianwu Dai, Boston, MA (US); Eugene Bell, Boston, MA (US); Vladimir Russakovsky, Boston, MA (US)

(73) Assignee: TEI Biosciences, Inc., Boston, MA (US)

( * ) Notice: Subject to any disclaimer, the term of this patent is extended or adjusted under 35 U.S.C. 154(b) by 273 days.

This patent is subject to a terminal disclaimer.

(21) Appl. No.: 10/770,296

(22) Filed: Feb. 2, 2004

(65) Prior Publication Data

US 2005/0013802 A1    Jan. 20, 2005

Related U.S. Application Data

(63) Continuation of application No. 09/871,518, filed on May 31, 2001, now Pat. No. 6,696,074.

(60) Provisional application No. 60/251,125, filed on Dec. 4, 2000.

(51) Int. Cl.
| A01N 1/02 | (2006.01) |
| A61F 2/00 | (2006.01) |
| C12N 11/02 | (2006.01) |
| C12N 5/06 | (2006.01) |
| C12N 5/08 | (2006.01) |

(52) U.S. Cl. .................. 435/1.3; 424/423; 424/93.7; 435/177; 435/395

(58) Field of Classification Search ............... None
See application file for complete search history.

(56) References Cited

U.S. PATENT DOCUMENTS

| 4,801,299 | A | | 1/1989 | Brendel et al. |
| 4,971,954 | A | * | 11/1990 | Brodsky et al. ............... 514/21 |
| 5,336,616 | A | | 8/1994 | Livesey et al. |
| 5,624,463 | A | | 4/1997 | Stone et al. |
| 5,756,678 | A | | 5/1998 | Shenoy et al. |
| 5,876,742 | A | * | 3/1999 | Cochrum et al. ........... 424/424 |
| 5,916,265 | A | | 6/1999 | Hu |
| 5,997,895 | A | | 12/1999 | Naratam et al. |
| 6,179,872 | B1 | | 1/2001 | Bell et al. |
| 6,379,615 | B1 | * | 4/2002 | Ogle ........................... 422/28 |
| 6,468,313 | B1 | * | 10/2002 | Claeson et al. .......... 623/23.72 |
| 6,696,074 | B2 | * | 2/2004 | Dai et al. .................... 424/423 |

OTHER PUBLICATIONS

International Search Report for PCT/US02/15620 (Jun. 17, 2003).
Darbord, "Inactivation of Prions in Daily Medical Practice," *Biomed & Pharmacother* 34:8 (1999).
Diringer et al., Infectivity of Unconventional Viruses in Dura Mater, *The Lancet*, 1:439-440 (1989).
U.S. Dept. Health and Human Services, "Guide for 510(K) Review of Processed Human Dura Mater," (1990) 2 FDA.
U.S. Dept. Health and Human Services, "Guidance for the Preparation of a Premarket Notification Application for Dura Mater," (1999) 6 FDA.

* cited by examiner

*Primary Examiner*—David M. Naff
(74) *Attorney, Agent, or Firm*—Fish & Richardson P.C.

(57) ABSTRACT

A method of forming and preserving a bioremodelable, biopolymer scaffold material by subjecting animal tissue, particularly fetal or neo-natal tissue, to chemical and mechanical processing. The process includes, but is not limited to, harvesting the tissue, optionally extracting growth and differentiation factors from the tissue, inactivating infective agents of the tissue, mechanically expressing undesirable components from the tissue, delipidizing the tissue, washing the tissue, optionally drying the tissue, optionally cross-linking the tissue not necessarily in the order described. The resulting product, EBM, is characterized by its microbial, fungal, viral and prion inactivated state. EBM is strong, bioremodelable, drapable and does not undergo calcification. EBM supplants previous inventions because of its unique method of preparation and broad applicability in tissue reengineering.

6 Claims, No Drawings

PROCESSING TISSUE TO PRODUCE A BIOPOLYMER SCAFFOLD FOR TISSUE ENGINEERING

CROSS-REFERENCE TO RELATED APPLICATIONS

This application is a continuation of, and claims the benefit of priority under 35 USC §120, of U.S. application Ser. No. 09/871,518, filed May 31, 2001, now U.S. Pat. No. 6,696,074 which is related to U.S. application Ser. No. 60/251,125, filed Dec. 4, 2000. The disclosure of the prior applications are considered part of (and are incorporated by reference in) the disclosure of this application.

BACKGROUND OF THE INVENTION

1. Field of the Invention

This invention relates to the field of tissue engineering, and in particular to a method of processing animal tissue including, particularly, fetal or neo-natal tissue to produce a biopolymer scaffold material named EB Matrix ("EBM"). EBM has broad applications for tissue repair and regeneration. It can serve as a remodelable scaffold for repair or replacement of human tissues and organs. It can be enriched with signaling molecules and cells before implantation, or with or without signaling molecules, it can attract host vessels and vascular cells as well as host parenchymal cells and immune systems cells to populate it after implantation. Also, it can serve as a delivery device for signaling factors, cells or drugs.

2. Description of the Related Art

Rebuilding the human body is a significant industry. Human tissue banks and synthetic polymers do not meet the need for repair or replacement of body parts. High on the list of alternative sources of material used to meet this need are animal tissues prepared in new ways that reduce their immunogenicity and maximize their usefulness and efficacy.

In the field of tissue engineering, the following three components are used alone or in combination to repair or create new tissue and organ substitutes. 1) scaffolds made of naturally-occurring polymers (e.g. collagens), man-made polymers, (e.g. PTFE, Dacron, PET or polyethylene) or self-degrading, man-made polymers (e.g. PLA or PGA); 2) signaling molecules that give developmental instructions to cells; and 3) cells having specific or multiple tissue building potential, often referred to as "stem cells". Here we describe biopolymer matrices, produced by novel methods, from animal tissues including fetal and neo-natal tissues to be used as tissue engineering scaffolds.

Man-made implant materials such as synthetic polymers, plastics, and surface-coated metals may have different degrees of immunogenicity and suffer from significant limitations that prohibit their broad applications. A major limitation is that cells cannot remodel them after implantation. They are highly susceptible to microbial infection, and some undergo calcification. Synthetic vascular conduits have a high incidence of occlusion after peripheral vascular bypass procedures.

There is a long history of the use of biopolymer matrices made from processed human or animal tissues. Several methods of preserving collagen-based matrices from animal tissues have been developed (U.S. Pat. No. 4,801,299, U.S. Pat. No. 5,336,616, U.S. Pat. No. 5,756,678, U.S. Pat. No. 5,916,265 and U.S. Pat. No. 5,997,895). All the methods include a chemical step that either kills or eliminates cells. Since tissues from post-natal animals or humans are the principal materials processed, a fixation step using glutaraldehyde or a similar agent may be used to mask antigenic determinants, eliminate the microbial burden and increase strength. However, aldehydic processing effectively destroys any biological activity, such as cell binding sites, associated with the original tissue and greatly reduces or eliminates the ability of cells to attach to it. It also eliminates binding sites for cell-synthesized products which attach to cells or to intermediates able to bind to cells and cell products that make up the extracellular matrix by cells.

Collagen-based devices that are animal-derived and fixed with glutaraldehyde or a similar agent can not be remodeled since they are highly resistant to metalloproteinase enzymes. Glutaraldehyde-treated devices are known to undergo gradual calcification. Heart valves made from fixed animal tissues can require replacement in 5-7 years or sooner due to calcification. The methods suggested in U.S. Pat. No. 4,801, 299 and U.S. Pat. No. 5,916,265 include the use of glutaraldehyde or a similar agent for the fixation of tissue derived from a post-natal animal source. The resulting products can not be faithfully remodeled.

While detergents or sodium hydroxide may be used to process post-natal animal tissue (U.S. Pat. No. 4,801,299, U.S. Pat. No. 5,336,616, U.S. Pat. No. 5,756,678, U.S. Pat. No. 5,916,265, U.S. Pat. No. 5,997,895), they have not been used to process fetal or neo-natal animal tissue. For example, U.S. Pat. No. 5,997,895, filed on Apr. 30, 1998, provides a certified collagen dural substitute derived from post-natal animal tissue that undergoes an alkaline/salt treatment involving sodium hydroxide and sodium sulfate (preferably in an aqueous solution of 5% sodium hydroxide and 20% sodium sulfate). A method for processing collagen containing materials which uses 1.0 N sodium hydroxide was disclosed in a journal article in 1989 by Diringer H. and Braig H. R. (Diringer H. and Braig H. R., 1989, Infectivity of unconventional viruses in dura mater. The Lancet, 439-440). This reference was cited in the FDA's *Guide for* 510(k) *Review of Process Dura Mater* (1990, 2).

The product of this invention, EBM, is unlike the other products cited above which in general are not bioremodelable. EBM is processed in a way that preserves its binding sites for cells and cell-secreted products that make up the extracellular matrix surrounding cells that occupy the scaffold. EBM is also distinguished by the fact that undesirable tissue components, such as DNA, are expressed mechanically from the tissue and that delipidyzing organic solvents are used to reduce the presence of cell and nuclear membranes. EBM does not calcify, making it safe for use in the human body for repair of soft tissues. In addition to its use for soft tissues, EBM can be used as a scaffold for bone repair if treated with an appropriate growth factor, if seeded with bone precursor cells or if occupied by bone forming cells when implanted.

EBM can be used as a tissue-building component with or without cells or signaling complexes for creating human body replacements. It can be used after the addition of signaling molecules, which will further promote tissue repair. It can also be implanted after stem or differentiated cells are seeded into or onto it.

BRIEF SUMMARY OF THE INVENTION

By processing animal tissue, including fetal or neo-natal tissue, by the method embodying the invention, tissue strength is preserved without reducing its intrinsic biological properties or compromising the ability of cells that occupy the tissue to remodel it. In addition to chemical processing, a step of mechanically expressing undesirable tissue components from the tissue is a significant innovation. Additionally, the uniqueness of this invention is that it includes the use of fetal or neo-natal tissue that, depending on age, is much less antigenic than adult tissue. The present invention overcomes the difficulties inherent in the approach to animal tissue use based on glutaraldehyde treatment.

DETAILED DESCRIPTION OF THE INVENTION

For convenience, certain terms used in the specification, examples, and appended claims are collected here alphabetically.

The term "bioremodelable" or "bioremodelability" refers to a material that lends itself to the breakdown by cells that occupy it and use it as a template for creating a replacement made up mainly of newly synthesized components secreted by the cells.

The terms "delipidizing" or "delipidized" refers to the removal of lipids from the tissue.

The term "DHT" refers to a dehydrothermal process, wherein the tissue is cross-linked and dehydrated at a high temperature.

The term "drapability" includes the capacity of the material to mold to irregular, curved surfaces or surfaces of other geometries.

The terms "inactivating" or "inactivated" refers to the reduction of the concentrations of infective agents (e.g. bacteria, molds, viruses and prions) by 4, 6 or 8 logs consistent with the requirements needed to insure against infectivity.

The phrase "mechanically expressing" refers to mechanically applying pressure to express undesirable components from the tissue. With the aid of appropriate solvents, unwanted components from the product that are potentially antigenic, such as DNA, RNA or other molecules released by reagents, such as NaOH, are removed.

The term "suturable" includes the ability to suture the material, wherein the material offers the required resistance to suture pull-out.

This invention involves preserving a naturally occurring, biopolymer-based matrix (EBM) from animal tissue, particularly fetal or neo-natal tissue. It provides a method of producing EBM, including the following steps: (1) removing the tissue from its source; (2) optionally extracting growth and differentiation factors from the tissue; (3) inactivating infective agents of the tissue; (4) mechanically expressing undesirable components from the tissue; (5) washing the tissue for removal of chemical residues; (6) optionallydrying; and (7) optionally cross-linking the tissue after chemical and mechanical treatment.

In the preferred embodiment, porcine or bovine tissues, including fetal and neo-natal tissues, are used. Preferably, for example the fetal bovine tissue source is between 10 weeks of age and newborn age. As an example, fetal bovine skin is flash frozen and stored. Other source material include blood vessels, other tubular structures, internal organs including the bladder, tendons, ligaments, cartilage, membranes such as the kidney capsule or diaphragm, or hard tissues such as cartilage or bone. After thawing, the tissue or organ is kept cold and chilled in an ice bath at a temperature between −4° C. and In a preferred embodiment, a salted ice bath is used to chill the tissue to a temperature below 0° C. The tissue adhering to the underside of the skin for example is mechanically removed.

Whereas, certain desirable naturally-occurring components of tissues, particularly fetal and neo-natal tissues, may be lost because of the harsh chemicals used for viral and prion inactivation and removal of unwanted structures and chemical components, some at high temperatures, desirable components such as growth and differentiation factors may be extracted from the skin or other tissue before the bleach and sodium hyrdroxide treatments for the purpose of viral and prion inactivation and for removal of unwanted structural and chemical components. In an alternative embodiment, growth and differentiation factors are extracted from the tissue by methods disclosed in U.S. Application No. 60/251,125, filed on Dec. 4, 2000, herein incorporated by reference (e.g. buffer, enzyme or acid extraction). The extracted growth and differentiation factors, being in solution, are treated much more mildly with the agents used for viral and prion inactivation, such as with 1 N sodium hydroxide for 4 hrs. on a shaker on ice. After treatment, the extracted growth and differentiation factors are returned to the skin or other tissue being processed which readily absorbs them.

In the preferred embodiment, the skin undergoes microbial, fungal, viral and prion inactivation, beginning with a treatment with bleach. The bleach is at a concentration of between 0.05% and 5%, and the time of treatment can vary between 1 minute and 5 hours. This step can also be done after the sodium hydroxide step described below. All solutions are chilled with ice or salted ice to a temperature between −4° C. and 10° C.

In the preferred embodiment, the tissue is washed extensively with water or physiological buffers (e.g. Tris-, HEPES, PBS buffer) to remove any residual bleach. The tissue is treated further with sodium hydroxide or potassium hydroxide at a concentration of between 0.1 N and 10 N for between 10 minutes and 2 hours. This treatment also inactivates infective agents of the tissue (e.g. bacteria, molds, viruses and prions). The container and all solutions are chilled with ice or salted ice to a temperature between −4° C. and 10° C. The container is subsequently placed on a shaker.

In the preferred embodiment, unwanted components from the tissue (e.g. DNA, RNA or other molecules released by reagents such as NaOH) are mechanically expressed by means of repeated applications of pressure using a flat blade (like a putty knife) and/or roller(s). The steps of mechanically expressing material dissociated from the tissue chemically can be carried out by a machine as well, through an operation similar to that used manually.

Any organic solvent as well as mixtures of them suitable for dissolving lipids may be used for removal of lipid materials (e.g. chloroform, acetone, ether, alcohols and their mixtures). In the preferred embodiment, the tissue is delipidized in a chloroform and ethanol mixture (1:1 concentration ratio) for between 5 minutes and 5 hours followed by washes in 70% ethanol and water, or the foregoing solvents can be used seriatim with the ethanol being at a concentration of 70% for similar periods of time applied after the chloroform step.

In the preferred embodiment, the tissue is subjected to extensive washing with distilled water or buffers until the chemical residue is removed. The final product that is designated as EBM, is stored in distilled water or buffers, or dried.

In an alternative embodiment, EBM can be cross-linked with genipin or DHT. If DHT is used, the tissue undergoes dehydration at a high temperature.

In an alternative embodiment, EBM can be freeze-dried by rapidly freezing the tissue and then dehydrating it in a high vacuum. Freeze-drying increases the porosity and flexibility of the tissue.

EXAMPLE 1

Preparation of EBM

To prepare the preferred embodiment of EBM, the following protocol is followed. All of the following steps are performed in a laminar-flow hood using aseptic techniques and sterile solutions.

A piece of fetal bovine skin is cut out and a mark is made to distinguish the sides. The piece of skin is approximately 25×20 cm in size and is free of pigment or holes. The skin is dipped in a beaker containing 2.0 liters of Mili-Q™ water to rinse off excess blood. The skin is placed epidermal side down on a flat, plastic plate. The skin is flattened onto the plate.

Flesh is removed from the under side (dermal side) of the skin using dissection tools, if done by hand; serrated tipped forceps are used to lift the flesh, and curved scissors are used to remove approximately 5-10 mm wide continuous strips of flesh from one end of the skin to the other end. Defleshing, then removal of epidermis from the outer side of the skin can also be done by a defleshing machine. If carried out manually, the process should continue as follows.

The skin is placed in 20% bleach for 30±3 minutes on ice. A 1.0 liter square, wide-mouth bottle with a screw cap containing 500±50 mls of bleach provides approximately 1.0 ml of solvent per $cm^2$ of skin. The temperature of the bleach is 4±2° C. The bottle is placed on a rocking platform. The skin is then washed in 2.0 liters of Mili-Q™ water for 20 minutes to dilute out the bleach.

The skin is placed on a flat, plastic plate epidermal side down. Any remaining subdermal flesh from the bottom side is removed with a flat blade like a putty knife by applying pressure to the blade as it is drawn over the surface of the tissue. This step mechanically expresses undesirable, chemically separated components from the tissue. The skin is held in place by a slip-resistant surface. The skin is turned epidermal side up and the epidermis is removed with a flat blade in strips of about 5.0 mm. A machine, through an operation similar to that used manually, can also perform the step of mechanically expression.

The skin is placed in a 5.2N solution of NaOH on a shaker on ice for 15±3 minutes. A 1.0 liter square, wide-mouth bottle with a screw cap containing 500±50 mls of NaOH provides approximately 1.0 ml of solvent per $cm^2$ of skin. The temperature of the NaOH is 4±2° C.

The NaOH step is repeated twice with mechanical expression carried out between the steps and after the second step. The concentration of NaOH and the time of exposure to the NaOH can be increased or decreased depending upon the thickness of the skin. This is followed by three washes in 1.0 liter of Mili-Q™ water for up to 20 minutes each and additional steps of mechanical expression as needed.

As stated before, any organic solvent, as well as mixtures from them, can be used for removal of lipid material. In the preferred embodiment, a 1:1 chloroform ethanol solution treatment is followed by a 70% ethanol wash. This is followed by two washes in 1.0 liter of Mili-Q™ water for up to 10 minutes each with additional steps of mechanical expression as needed.

EBM is immersed in 1.0 liter of sterile PBS (phosphate buffered saline) for 20+4 hours on a rocking platform at a temperature of 4±2° C. which provides approximately 2.0 ml of PBS per $cm^2$ of skin.

EBM may be air-dried between two porous plates with or without the application of pressure for 24 hours. If increased porosity is desired, EBM can be freeze-dried.

EXAMPLE 2

5 Use of EBM

EBM made from skin tissues can be used as a skin wound dressing or a skin replacement tissue. With or without the addition of signaling molecules and cells, EBM promotes wound healing. EBM is suitable for the treatment of chronic topical wounds such as burns, ulcers, and avulsion injuries. In grafts to host animals, such as rats, to replace full thickness skin wounds, acellular EBM is shown to remodel to replacement skin without scaring. However, secondary derivatives are absent. If seeded with dermal fibroblasts and keratinocytes, EMB can serve as a living skin replacement.

EBM can be used as a repair or replacement device throughout the human body.

For example, EBM can be used as a urethral sling because of its high physical strength, resistance to stretch, suturability, cell-compatibility and bioremodelability.

EBM produced from fetal or neo-natal animal skins (e.g. porcine skin, bovine skin) can also be used for pericardial, periosteal, rotator cuff, or dura repair or replacement, or for hernia repair. It is drapable and has single suture-pullout strength of more than 20 Newtons.

EBM can be homogenized for use in an injectable form or as a foam in hemostats, dura replacement, and other similar areas of treatment. The same or similar processing described in the example above can be applied to non-skin tissues of the body to provide scaffolds of replacement parts with or without the addition of cells, signaling complexes or drugs, with the expectation that if acellular or cellular they will be vascularized and populated with host cells.

This disclosure is not limited to preserving EBM derived from those tissues or organs described herein. EBM may be derived from a wide variety of tissues and organs.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

The invention claimed is:

1. A method for producing a biopolymer scaffold, comprising:
    (a) providing tissue from an animal;
    (b) treating the tissue with KOH or NaOH;
    (c) applying pressure to the tissue to release components disassociated from the tissue by treatment with KOH or NaOH;
    (d) rinsing the tissue in aqueous solution;
    (e) treating the tissue with organic solvents to delipidize the tissue;
    (f) applying pressure to the tissue to release components disassociated from the tissue by treatment with organic solvents; and
    (g) rinsing the tissue in an aqueous solution.

2. The method of claim 1, wherein the tissue is bovine.

3. The method of claim 1 wherein treatment with organic solvents comprises treatment with a solution comprising a solvent selected from the group consisting of: chloroform, acetone, ether, alcohols, and mixtures thereof.

4. The method of claim 1 wherein treatment with organic solvents comprises treatment with a mixture of chloroform and ethanol.

5. The method of claim 1 wherein the tissue is rinsed with an aqueous alcohol solution after treatment with organic solvents.

6. The method of claim 1 further comprising:
    (h) freeze drying the tissue.

* * * * *